(12) United States Patent
Einbond et al.

(10) Patent No.: US 9,643,995 B2
(45) Date of Patent: May 9, 2017

(54) TRITERPENE GLYCOSIDE AND TRITERPENE COMPOSITIONS AND METHODS OF USING SAME

(71) Applicant: Research Foundation of the City University of New York, New York, NY (US)

(72) Inventors: Linda Saxe Einbond, Crestwood, NY (US); Krishnaswami Raja, Staten Island, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 269 days.

(21) Appl. No.: 14/158,616

(22) Filed: Jan. 17, 2014

(65) Prior Publication Data

US 2014/0199297 A1    Jul. 17, 2014

Related U.S. Application Data

(60) Provisional application No. 61/753,714, filed on Jan. 17, 2013, provisional application No. 61/904,839, filed on Nov. 15, 2013.

(51) Int. Cl.

| | | |
|---|---|---|
| *A61K 31/74* | (2006.01) |
| *C07J 71/00* | (2006.01) |
| *A61K 31/337* | (2006.01) |
| *A61K 31/58* | (2006.01) |
| *A61K 47/48* | (2006.01) |
| *C07K 16/32* | (2006.01) |
| *A61K 45/06* | (2006.01) |
| *A61K 39/395* | (2006.01) |

(52) U.S. Cl.
CPC ......... *C07J 71/0005* (2013.01); *A61K 31/337* (2013.01); *A61K 31/58* (2013.01); *A61K 39/39558* (2013.01); *A61K 45/06* (2013.01); *A61K 47/48907* (2013.01); *C07K 16/32* (2013.01)

(58) Field of Classification Search
CPC .. A61K 39/00; A61K 39/39558; A61K 45/00; A61K 45/06; A61K 47/00; A61K 47/48907; A61K 31/00; A61K 31/337; A61K 31/58; C07J 71/0005; C07K 16/32
USPC ...... 424/1.11, 1.49, 1.65, 9.1, 9.2, 400, 417; 514/1, 19, 2, 19.3, 19.4, 19.5, 19.6; 977/773
See application file for complete search history.

(56) References Cited

PUBLICATIONS

Raja et al. "Hybrid Virus-Polymer Materials. 1. Synthesis and Properties of PEG-Decorated Cowpea Mosaic Virus," Biomacromolecules, 4:472-476 (Mar. 27, 2003).

Cirstoiu-Hapca et al. "Nanomedicines for active targeting: Physicochemical characterization of paclitaxel-loaded anti-HER2 immunonanoparticles and in vitro functional studies on target cells," European Journal of Pharmaceutical Sciences 38:230-237 (Jul. 24, 2009).

(Continued)

*Primary Examiner* — D L Jones
(74) *Attorney, Agent, or Firm* — Hoffmann & Baron, LLP

(57) ABSTRACT

In the present invention, different strategies are used to improve the bioavailability of triterpene glycosides and triterpenes including, for example, (a) a covalent approach involving modification with polyethylene glycol and (b) a formulation approach involving non-covalent encapsulation in antibody targeted pol(DL-lactic acid) nanoparticles.

8 Claims, 8 Drawing Sheets

(56) References Cited

PUBLICATIONS

O'Shannessy et al. "Folate receptor alpha (FRA) expression in breast cancer: identification of a new molecular subtype and association with triple negative disease," SpringerPlus, 1:22 (2012).
Akbarzadeh et al. "Liposome: classification, preparation, and applications," Nanoscale Research Letters, 8:102 (2013).
Li et al. "Liposome-Encapsulated Curcumin: In Vitro and In Vivo Effects on Proliferation, Apoptosis, Signaling, and Angiogenesis," Cancer 104:1322-1331 (Aug. 9, 2005).

Fig. 2B Effect of actein on Her2 and p-Her2

TRITERPENE GLYCOSIDE AND TRITERPENE COMPOSITIONS AND METHODS OF USING SAME

CROSS-REFERENCE TO RELATED APPLICATION

This application claims the benefit of U.S. Provisional Application No. 61/904,839, filed Nov. 15, 2013, and U.S. Provisional Application No. 61/753,714, filed Jan. 17, 2013, both of which are incorporated herein by reference in their entireties.

BACKGROUND OF THE INVENTION

Breast cancer is the second most common type of cancer worldwide. The American Cancer Society's estimates for breast cancer in the United States for 2013 are: about 232,340 new cases of invasive breast cancer will be diagnosed in women, and about 39,620 women will die from breast cancer.

The scientific and technical advances in breast cancer treatment have entailed a large cost. The treatment of breast cancer consumes a large part of the healthcare budget: (2005) 15-20% of all cancer costs and 1% of the total healthcare budget (Lamerato et al., 2006). The economic burden for the year 2001 was $15-20 billion (Campbell and Ramsey, 2009). The lifetime per patient costs of breast cancer range from $20,000 to $100,000.

Efforts to develop effective prevention and treatment of this disease have fallen short. For example, current treatments employ toxic agents that cannot be targeted to the affected cells. Additionally, the efficacy of pharmaceuticals and herbal extracts/components is limited by bioavailability. Treatments that can surmount these shortcomings are thus of high priority.

SUMMARY OF THE INVENTION

A limitation of using hydrophobic natural products directly as drug candidates is poor water and plasma solubility and consequently low bioavailability. Additionally, these natural products are not targeted, thereby potentially leading to toxic effects. The present invention overcomes toxicity and bioavailability problems associated with the herbal compounds of triterpene glycosides and triterpenes.

In the present invention, different strategies are used to improve the bioavailability of triterpene glycosides and triterpenes including, for example, (a) a covalent approach involving modification with polyethylene glycol and (b) a formulation approach involving non-covalent encapsulation in antibody targeted pol(DL-lactic acid) nanoparticles.

In one embodiment, A PEGylated triterpenes glycoside or triterpene with improved bioavailability is provided with the following formulae

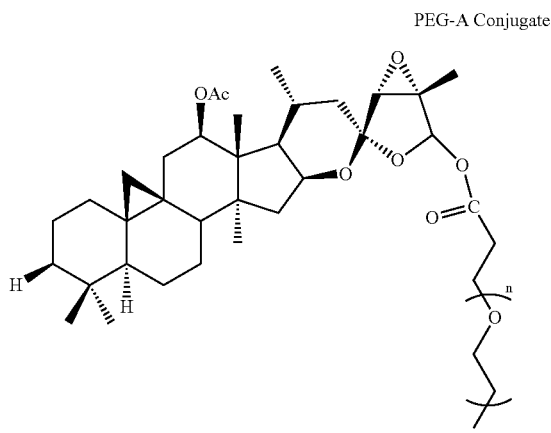

PEG-A Conjugate

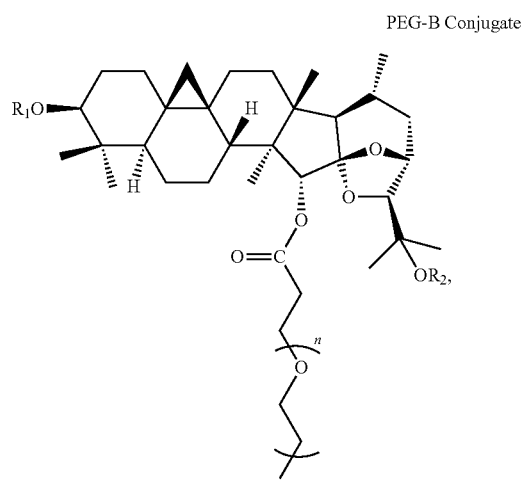

PEG-B Conjugate wherein R is OH or H, and wherein R1 is α-L-arabinoside and R2 is H, R1 is β-D-xyloside and R2 is H, or R1 is β-D-xyloside and R2 is Ac.

In one aspect, the present invention provides a method of treating and/or inhibiting cancer, and/or other inflammatory disorders, by the administration of the PEGylated triterpenes glycosides or triterpenes to a patient in need thereof. A chemotherapeutic agent can optionally be administered. Examples of chemotherapeutic agents include taxol and Herceptin.

In another embodiment of the present invention, nanoparticles coated with cancer-cell targeted antibodies are provided. An example of such nanoparticle is

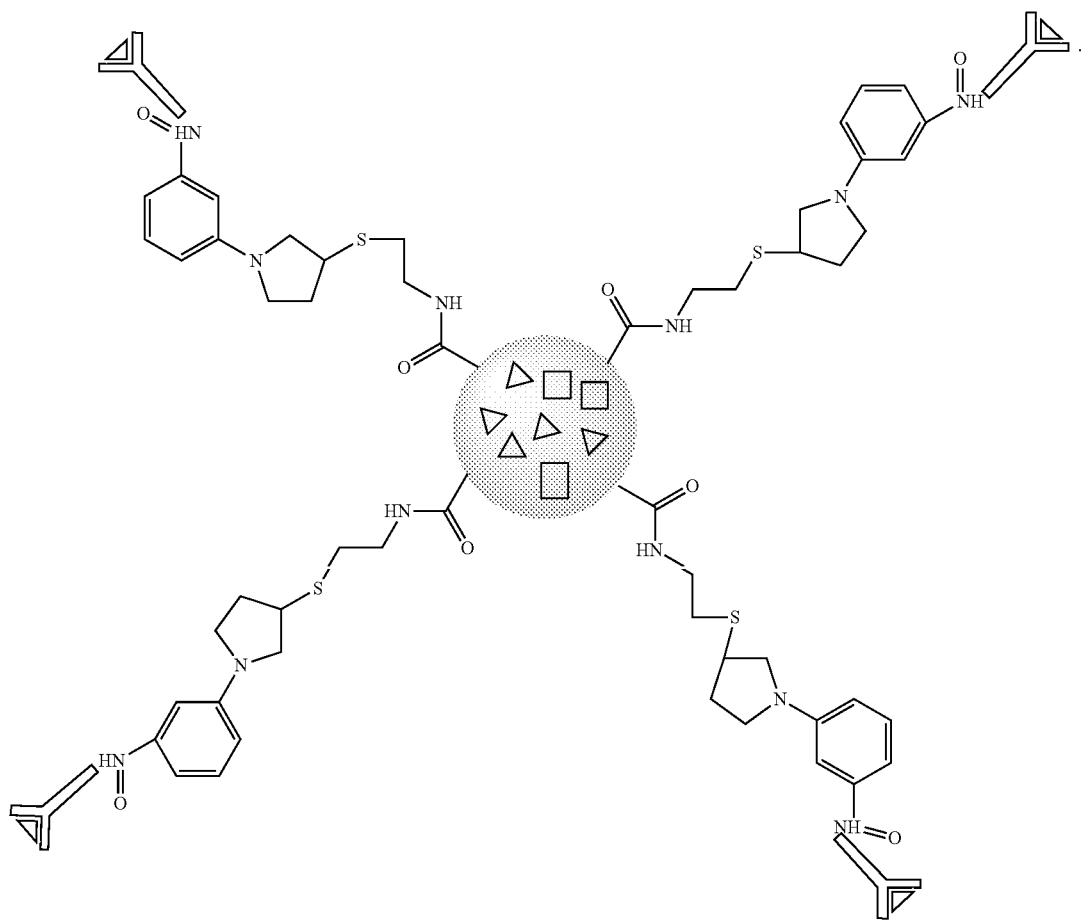

☐ = Chemotherapeutic Agent

▷ = titerpene glycoside or triterpene wherein

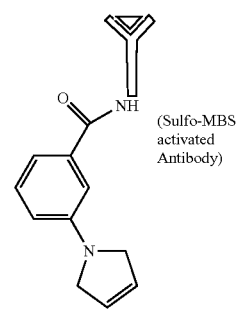

(Sulfo-MBS activated Antibody)

In these nanoparticles, the triterpenes glycoside or triterpene is optionally PEGylated.

In one aspect, the present invention provides a method of treating and/or inhibiting cancer, and/or other inflammatory disorders, by the administration of the coated nanoparticles to a patient in need thereof. An additional chemotherapeutic agent can optionally be administered.

Some of the advantages of the present invention over current cancer therapies, include the following: 1) relatively nontoxic, triterpene glycosides and triterpenes, e.g., actein derivatives; 2) nanoparticle technology; 3) techniques for coating nanoparticles with the cancer-cell targeted antibodies, e.g., Herceptin, to enhance potency; 4) synergy is among triterpene glycosides and triterpenes (e.g., actein), Herceptin, and nanoparticles, thus targeting multiple pathways, with minimal toxicity. These therapies can be combined with chemotherapeutic agents.

DETAILED DESCRIPTION OF INVENTION

Figure 1:
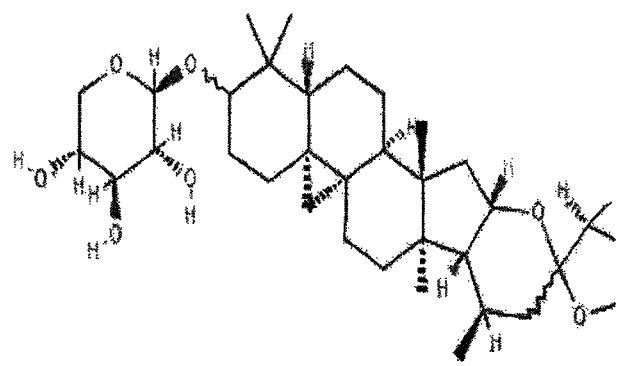
FIG. 1 is a structural depiction of actein.

The present invention relates to pharmaceutical compositions for treating and preventing diseases and disorders, including, for example, cancer and inflammatory disorders, and methods of treating such diseases and disorders.

A pharmaceutical composition of the present invention comprises a physiologically effective dose of a triterpene glycoside or a triterpene with enhanced bioavailability.

Preferred examples of triterpene glycoside compounds include actein, 23-epi-26-deoxyactein, cimiracemoside C, cimigenoside, 25-acetylcimigenol xylopyranoside, cimifugoside, cimigenol glycoside, and cimiracemoside A. Actein preferentially inhibits the growth of malignant, but not nonmalignant cells. In addition, actein synergizes with chemotherapeutic agents, such as, e.g., Herceptin and paclitaxel. A preferred example of a triterpene compound is cimigenol.

In the present invention strategies to improve the bioavailability of triterpene glycosides and triterpenes include covalent approaches involving modification with polyethylene glycol and formulation approaches involving non-covalent encapsulation in antibody targeted poly(DL-lactic acid) nanoparticles.

In one embodiment of the present invention, a triterpene glycoside or triterpene is modified with polyethylene glycol, i.e., PEGylated. For example, a triterpene glycoside or triterpene is PEGylated by covalently modifying the reactive hydroxyl group in Compound A or B with polyethylene glycol as follows:

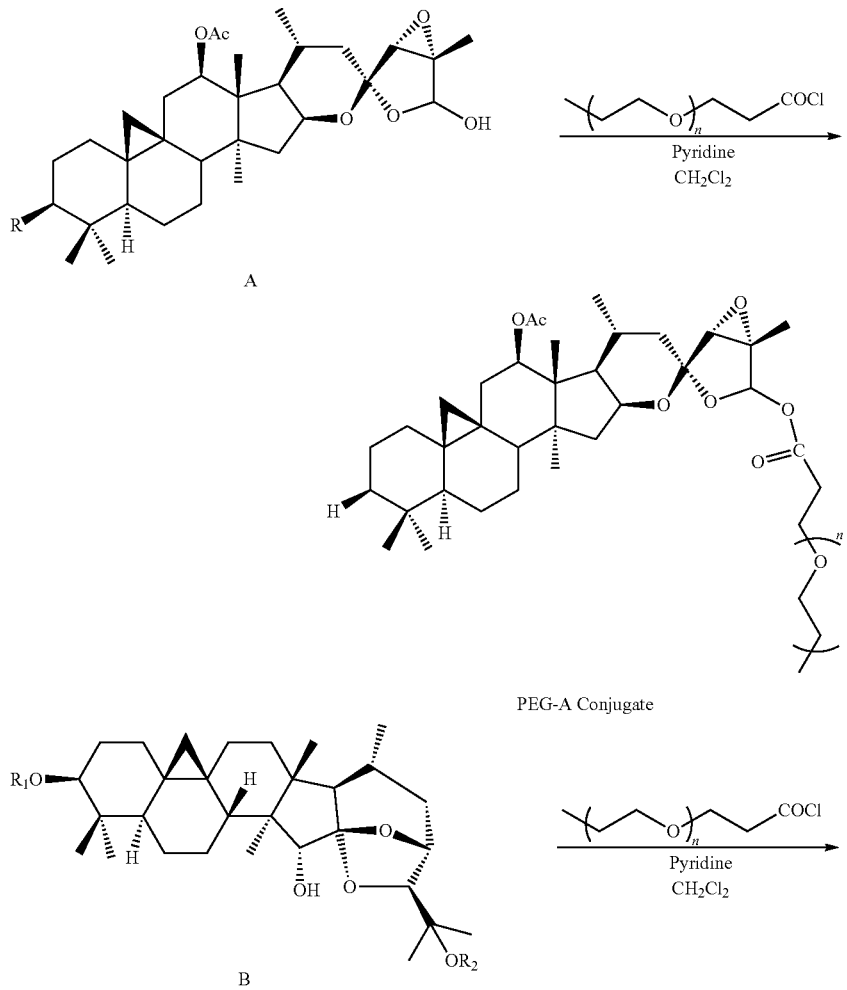

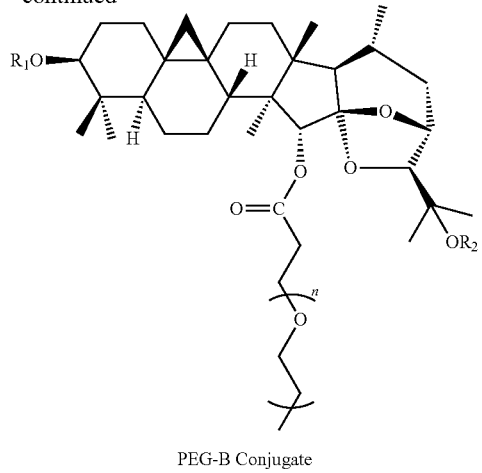

PEG-B Conjugate
20 wherein R is OH or H, and wherein R1 is α-L-arabinoside and R2 is H, R1 is β-D-xyloside and R2 is H, or R1 is β-D-xyloside and R2 is Ac.

In a further embodiment, liposomes encapsulate the active compounds. A description of such liposomes is found in U.S. application Ser. No. 13/694,335, incorporated herein by reference. Such liposomes are PEGylated by the methods of the present invention. PEGylated liposomes resist uptake by macrophages resulting in a longer circulation time.

The PEGylated liposomes are preferably fusogenic. For example a suitable liposome is composed of dioleoyl phosphatidylethanolamine (DOPE) and dioleoyl phosphatidylcholine (DOPC). Liposomes can also be prepared using other types of lipids, such as, for example, 1,2-Dimyristoyl-sn-glycero-3-phosphocholine (DMPC) and (DMPC/DMPG) (DMPG=1,2-dimyristoyl-sn-glycero-3-[phospho-rac-(1-glycerol)] [sodium salt]). Preferred PEGylated liposomes (stealth liposomes) include DOPC: DSPE-mPG2000.Na (95:5). (DSPE-mPG2000.Na is 1,2-distearoyl-sn-glycero-3-phosphoethanolamine-N-[amino(polyethylene glycol)-2000] (ammonium salt) (Avanti Polar Lipids: Catalog Number: 880128 Name: DSPE-PEG (2000)).

The ratio of total lipid to the active compound (weight/weight) can range from approximately 20:1 to approximately 2:1, or from approximately 15:1 nm to approximately 3:1, or from approximately 10:1 to approximately 4:1. As a specific example, a preferred PEGylated liposome complex is composed of DOPE:DOPC:Actein in 40:50:10 molar ratio in PBS buffer sized to 100 nm.

Chemopreventive and chemotherapeutic agents can also optionally be added to the liposomes. For example, for combinations, a [lipo-active compound] and a [lipo-chemotherapeutic agent] can be mixed using a 3-way adjuvant mixer.

In another embodiment, a triterpene glycoside or triterpene is non-covalently encapsulated in antibody-targeted nanoparticles to produce a chemotherapeutic formulation. In such embodiment, poly(DL-lactic acid) nanoparticles loaded with a triterpenes glycoside or triterpene is provided. The nanoparticles are modified to produce nanoparticles with thiol groups. A sulfo-maleimidobenzoyl-N-hydroxy sulfosuccinimide ester activated antibody is conjugated to the thiol groups. Preferably, the antibody is anti-Her2. The nanoparticles can optionally be further loaded with a taxoid. Optionally, the triterpenes glycoside or triterpene is PEGylated.

Figure 3:
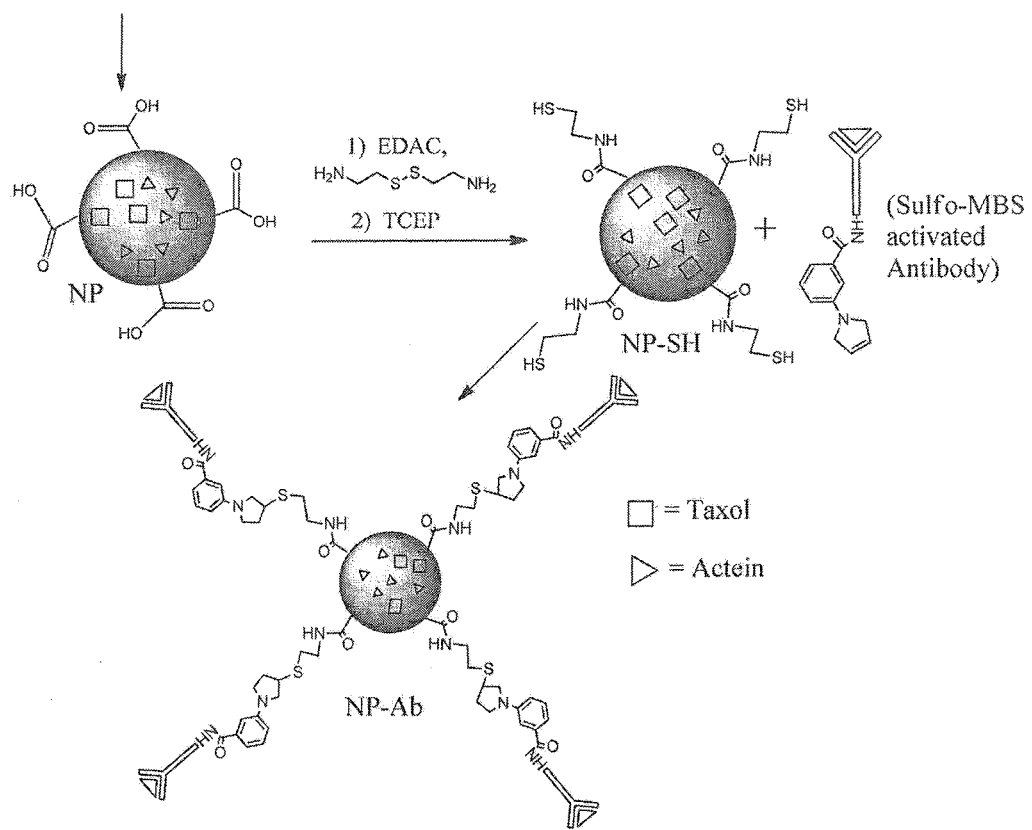
FIG. 3 is a depiction of a scheme for the synthesis of antibody targeted actein and or taxol loaded PLGA-Ab nanoparticles (NP-Ab) (Scheme 2).
Figure 4:
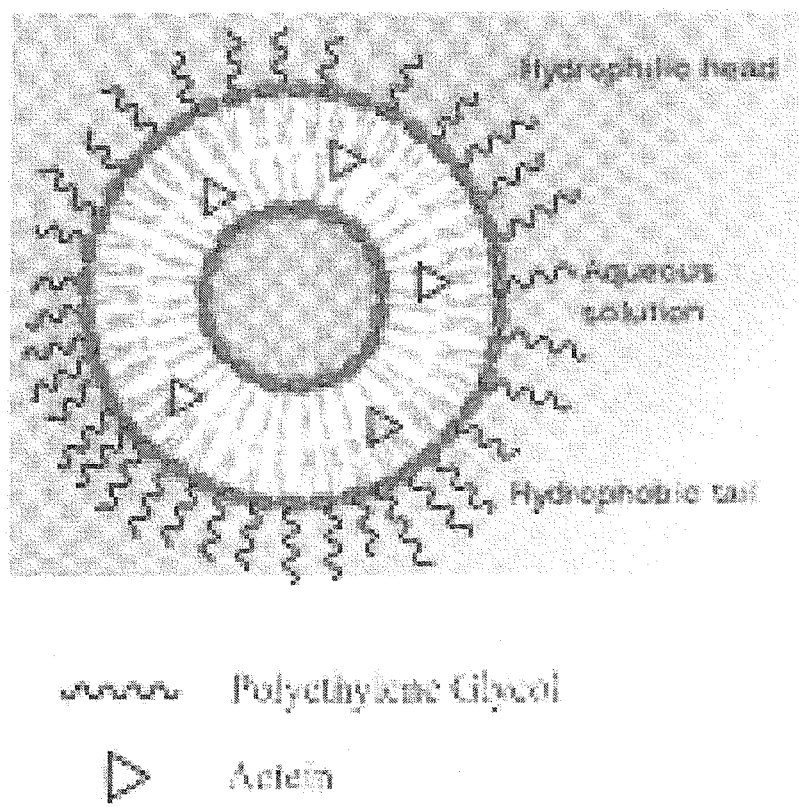
FIG. 4 is a representation of Actein loaded PEGYlated liposome.
Figure 5:
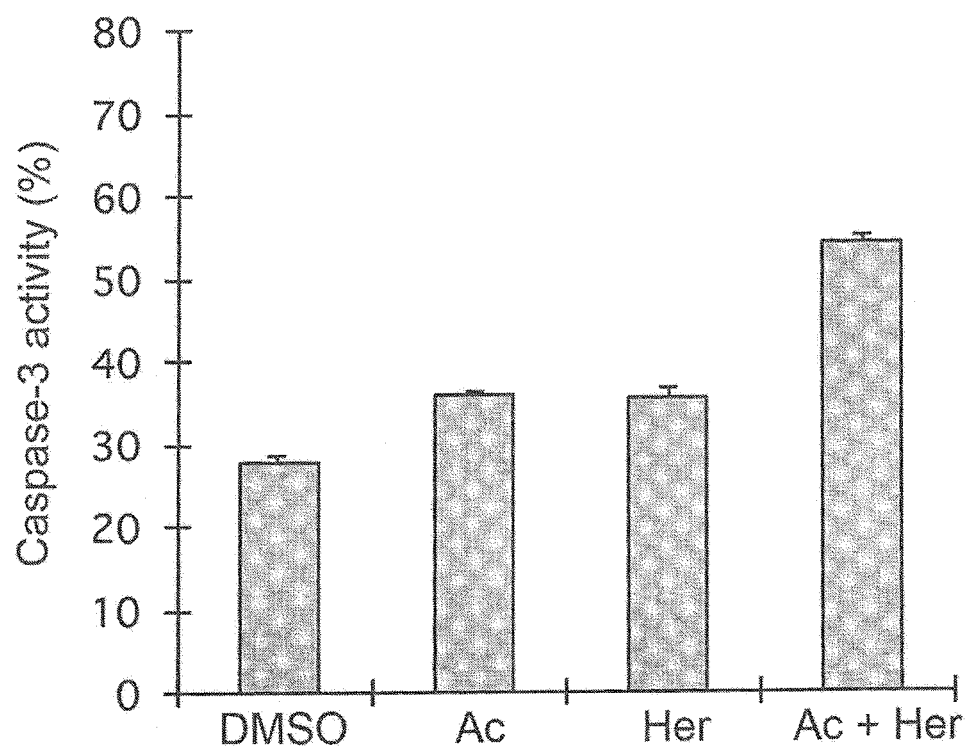
FIG. 5 is a graph depicting the effect of actein on capase 3 activity.
Figure 6:
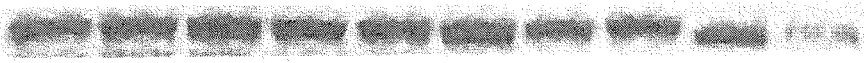
FIG. 6 is a Western blot analysis of the effect of actein on the level of Her2 and activated Her2 protein.
Figure 7:
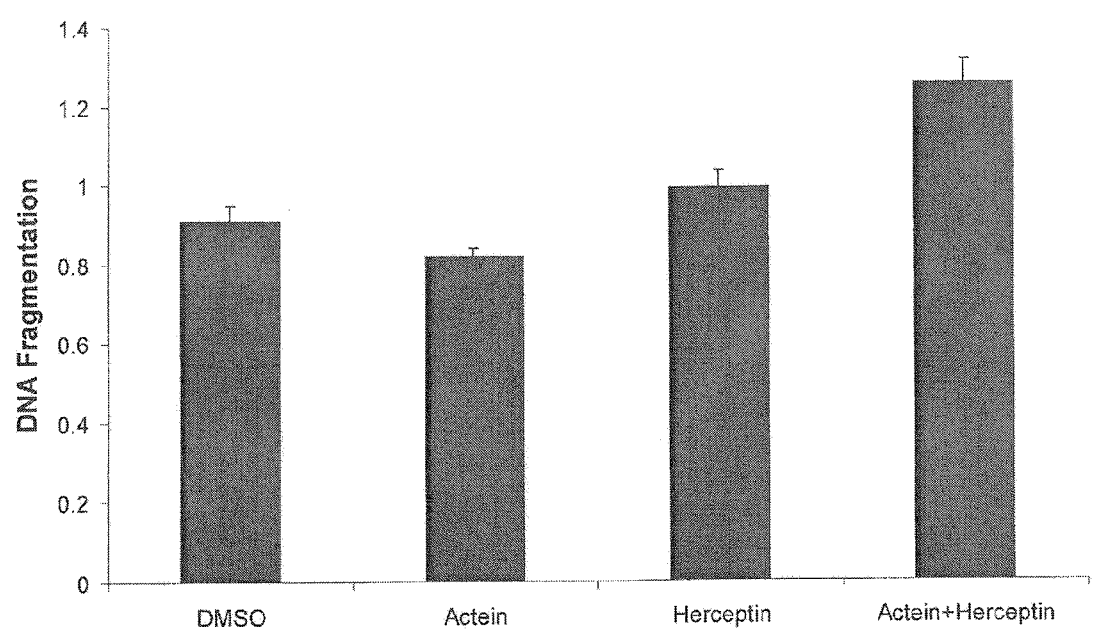
FIG. 7 is a graph showing the effect of actein on DNA fragmentation.

In a preferred embodiment, the nanoparticles with thiol groups are produced by contacting the nanoparticles with cystamine and 1-ethyl-3-(3-dimethylaminopropyl)-carbodiiminde (EDAC) and a reducing agent. See FIG. 3.

In one aspect, present invention, provides methods of treating and preventing diseases and disorders. Preventing a diseases or disorder includes inhibiting and/or reducing the possibility of contracting a disease or disorder. The methods comprise systemic administration of the pharmaceutical compositions of the present invention to a mammal in need thereof. Systemic administration includes oral, intramuscular, intraperitoneal, subcutaneous and intravenous administration. Typically, the mammal is a human.

The pharmaceutical compositions of the present invention can be administered to treat and prevent cancer, for example, breast, prostate, oral, skin, colon and liver cancers. The compositions are particularly effective to treat breast and colon cancers. Treating includes inhibiting the growth of cancerous tumors.

Two major signaling pathways found in breast cancer cells are: the ER-mediated signaling pathway exemplified in the estrogen-dependent human breast cancer cell line MCF7 and the ER-negative Her2-mediated signaling pathway in the estrogen-independent human breast cancer cell line MDA-MB-453 which overexpresses Her2 (erb2, c-neu), a membrane-associated tyrosine kinase receptor. This invention comprehends targeting ER positive, as well as ER negative breast cancer, since actein preferentially targets Her2 overexpressing human breast cancer cells, which develop harder to treat and more aggressive tumors. The methods of the invention are particularly suited to treat ER+, HER+ and HER2+ breast cancer types.

Without wanting to be bound by a mechanism, it is believed that a mode of action of actein is as follows: 1) actein at low concentrations (100 nM) immediately opens calcium channels and releases calcium from cells; 2) actein encapsulated in liposomes is highly potent on human breast cancer cells (.about.4-fold increase in activity).

In treating cancer, the pharmaceutical compositions of the present invention can synergistically be administered with chemopreventive and chemotherapeutic agents. Examples of such agents include paclitaxel, doxorubicin, 5-FU, Herceptin, tamoxifen, sulindac sulfide, thapsigargin and MEK inhibitor U0126. A particular synergistic result has been seen for the administration of actein in combination with paclitaxel and/or Herceptin to treat Her2 type breast cancer.

The chemopreventive agents and chemotherapeutic agents can be co-administered with the pharmaceutical compositions as a separate composition. Alternatively, the agents can coat the nanoparticle complexes of the invention.

The pharmaceutical compositions of the present invention target anti-inflammatory pathways. Thus, the compositions can be used to treat and prevent, and mediate the effects of inflammatory diseases, including, for example, cardiovascular and lipid disorders.

The pharmaceutical compositions of the present invention also have anti-HIV, statin, and osteoprotective effects. Methods of treating related disorders are included in the present invention.

The pharmaceutical compositions may be administered intermittently. For example, depending on the dose and the disease, the pharmaceutical compositions may be administered 1-6 times a day, preferably 1-4 times a day, as would be known to a skilled artisan.

Alternatively, the pharmaceutical compositions may be administered by sustained release. Sustained release administration is a method of drug delivery to achieve a certain level of the drug over a particular period of time. The level typically is measured by serum concentration.

For the pharmaceutical purposes described above, the compositions of the invention can be formulated per se in pharmaceutical preparations optionally with a suitable pharmaceutical carrier (vehicle) or excipient as understood by practitioners in the art. These preparations can be made according to conventional chemical methods.

For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums, glycols, buffers (e.g., PBS), and other pharmaceutically acceptable solvents.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the pharmaceutical compositions can be employed, and the pH of the solutions can be suitably adjusted and buffered. For intravenous use, the total concentration of the solute(s) can be controlled in order to render the preparation isotonic.

The pharmaceutical compositions of the present invention can further comprise one or more pharmaceutically acceptable additional ingredient(s) such as alum, stabilizers, buffers, coloring agents, flavoring agents, and the like.

Thus, while there have been described what are presently believed to be the preferred embodiments of the present invention, other and further embodiments, modifications, and improvements will be known to those skilled in the art, and it is intended to include all such further embodiments, modifications, and improvements and come within the true scope of the claims as set forth below.

EXAMPLES

Studies of the Inventors Delineate the Mode of Action of Actein

Preferential effect on malignant cells: The nonmalignant human mammary epithelial cell line MCF10F was considerably less sensitive to actein; the $IC_{50}$ values were 42 µg/ml for MCF10F vs.14 µg/ml for MF7 cells.

Figure 8:
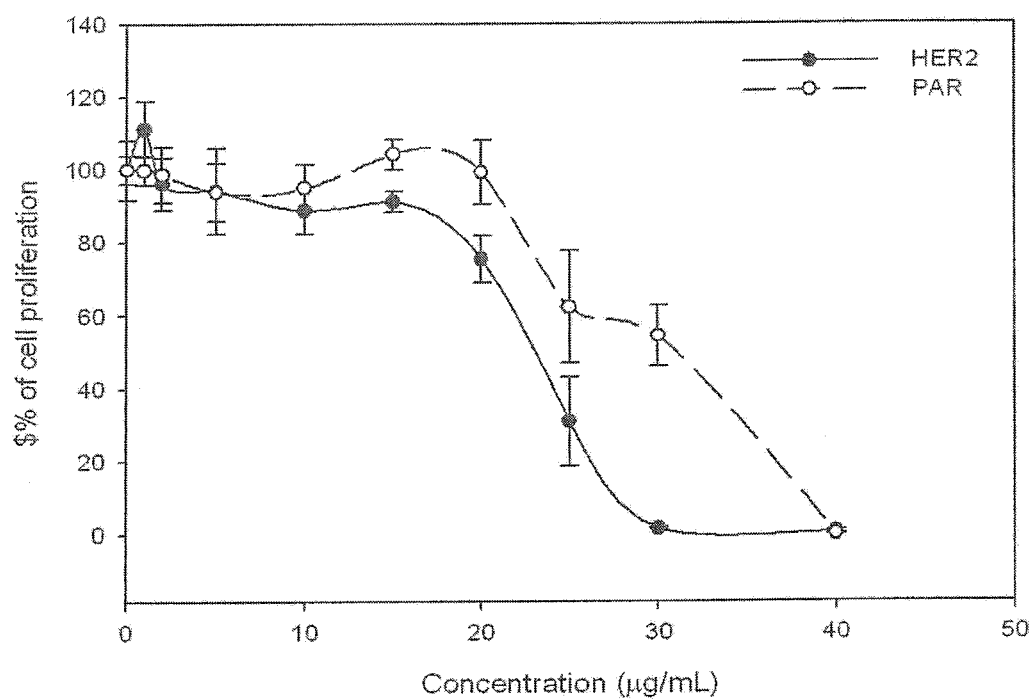
FIG. 8 is a graph showing the effect of actein on cell proliferation in MCF7 (Her2) and MCF7 human breast cancer cells. Cells were treated with increasing concentrations of actein for 96 hrs and the number of viable cells determined using the MTT assay.
Figure 9:
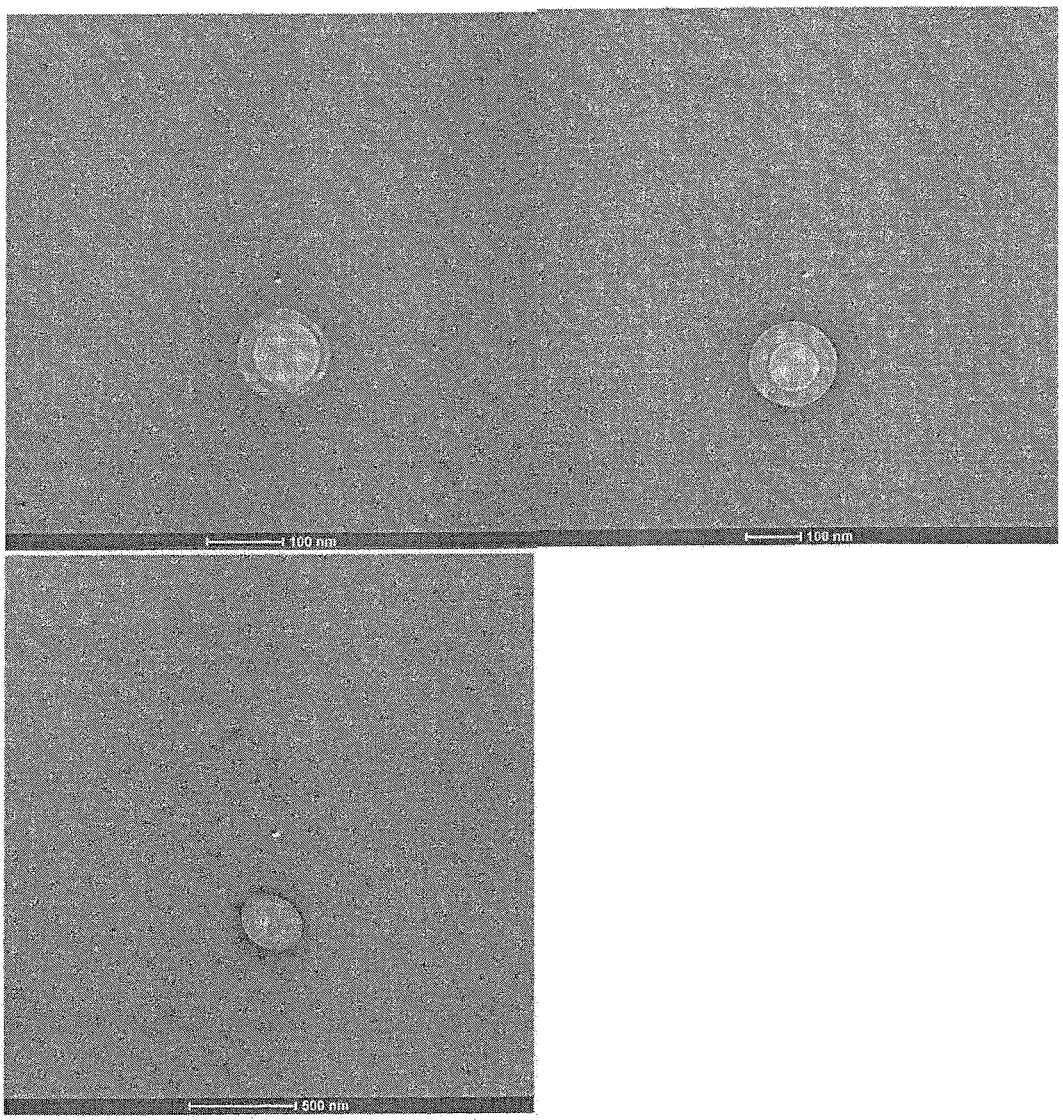
FIG. 9 is a Transmission Electron Microscopy of Poly (lactic acid) Nanoparticles: Lyophilized nanoparticles were suspended in 95% ethanol and a 3 μL drop was placed on a copper TEM grid with a carbon coating. The nanoparticles were imaged on a Fei Tecnai Spirit Transmission Electron Microscope at 100 kilovolts without any contrast enhancing agents. There are at least two different populations of nanoparticles with different characteristic sizes and morphologies. (a & b) belong to a population with a length slightly greater than 100 nm, (c) comes from a population with a length of approximately 300 nm.

The role of Her2 in the antiproliferative effects of black cohosh extract on human breast cancer cells: It was determined that actein is an active component of black cohosh and its activity is related to the expression of the Her2 receptor. Since Her 2 overexpressing breast cancers develop harder to treat and more aggressive tumors, the effect of actein was tested on the genetically matched pair of cells MCF7 and MCF7 transfected with Her-2. It was found that the Her2 transfected cells ($IC_{50}$ value: 22 µg/ml; 32.5 µM) are more sensitive than the parental cells ($IC_{50}$ value: 31 µg/ml; 45.8 µM) (data not shown). (See FIG. 8.) This indicates that Her2 plays a role in the action.

Figure 2:
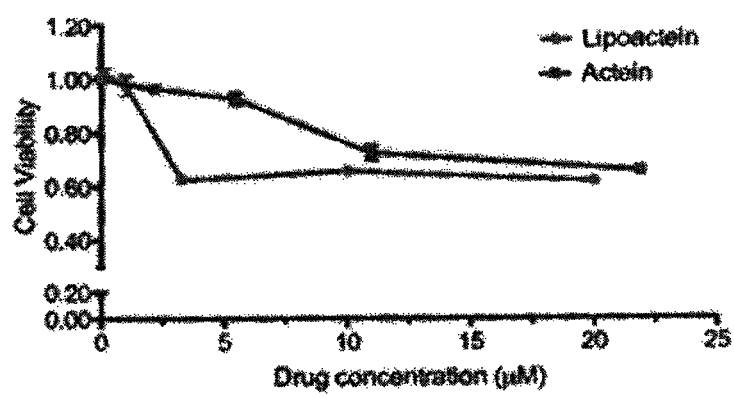
FIG. 2 is a graph showing the growth inhibitory effects of liposome-actein (Lipo-actein) compared to actein on MCF7 human breast cancer cells. At 22 h after treatment, MTT was added. The $IC_{50}$ values would be higher if MTT would have been added at 96 h.

Nanoparticle actein: As proof of principle, actein encapsulated in liposomes (lipo-actein) (fusogenic liposomes composed of DOPE:DOPC:actein in 40:50:10 molar ratio in PBS buffer sized to 200 nm; Encapsula NanoScience; Nashville, Tenn.) was prepared and the growth inhibitory effect on MCF7 human breast cancer cells was tested. Lipo-actein is significantly more active than actein on MCF7 cells (actein at 11 µM is less active than Lipo-actein at 3.2 µM). (See FIG. 2.)

Synergistic effects of actein in combination with paclitaxel or Herceptin: Actein alone, and in combination with chemotherapy agents, was tested for growth inhibition of the ER-Her2 overexpressing breast cancer cell line MDA-MB-453. It was found that actein exerted a synergistic effect when combined with paclitaxel or Herceptin. Paclitaxel was used since it is frequently used in the treatment of breast cancer. Moderate synergy (CI 2+) was seen with as little as 1 µg/mL of actein and 1 nM paclitaxel, and strong synergy (CI 3+) with 10 µg/mL actein and 1 nM paclitaxel. Herceptin is also used in the treatment of Her2 positive breast cancers (Pegram et al., 1999). Since the MDA-MB-453 cells were relatively resistant to Herceptin (Yakes et al., 2002) the effect of actein in combination with Herceptin was tested on the BT474 breast cancer cell line that expresses a high level of HER2. A 3+ synergistic effect was seen with 0.4 µg/mL actein plus 54 nM (8 µg/mL) Herceptin. Thus relatively low concentrations of actein can cause synergistic inhibition of human breast cancer cell proliferation when combined with the taxane paclitaxel and the antibody to Her2 Herceptin. A combination of the three agents is therapeutic for ER negative breast cancer.

Synthesis of Active Derivatives and Nanoparticles that Target Malignant Tissues.

One of the major limitations of using hydrophobic natural products directly as drug candidates is poor water and plasma solubility and consequently low bioavailability. The processes of the present invention include different strategies to improve the bioavailability of actein: (a) a covalent approach involving modification with polyethylene glycol and (b) a formulation approach involving non-covalent encapsulation in antibody targeted poly(DL-lactic acid) nanoparticles.

Synthesis of Potent Derivatives of Actein and Related Triterpene/Triterpene Glycosides from Black Cohosh by Making PEGylated Derivatives.

Covalent PEGylation Strategy

Polyethylene glycol [PEG] is a water soluble non immunogenic FDA Generally Regarded As Safe (GRAS) polymer, the attachment of PEG to molecules (referred to as PEGylation) is a standard method employed to improve water/plasma solubility and enhance the bioactivity of drug candidates (Raja et al., *Biomacromolecules*, 2003, 4(3):472-476.; Hermenson, G. T. *Bioconjugate Techniques*, Academic Press, 1996).

In the present invention, there is a covalent modification of the reactive hydroxyl group present in compounds A and B with commercially available PEG reagents in accord with Scheme 1. An important aspect of this strategy is that the ester linkages connecting A and B to the PEG moieties are hydrolyzed by cytosolic esterases, thereby releasing free drug inside the target cells (Langone et al., *International Journal of Cancer* 2012, 131(4):E569-78). The aglycone can be obtained by the hydrolysis of actein with cellulase (Sigma; Onorato and Henion, 2001). Onorato et al., Anal Chem. 2001 Oct. 1; 73(19):4704-10. PMID: 11605850

A series of conjugates with varying PEG chain length was synthesized and screened to arrive at the construct with maximum bioefficacy. This molecule is evaluated in vitro and compared with the parent molecule (Dolai et al., 2011; Parvathy et al., 2009). All the conjugates were characterized by NMR, IR, and Mass spectroscopy.

Scheme 1.
Black Cohosh derivatives with enhanced water/plasma solubility.
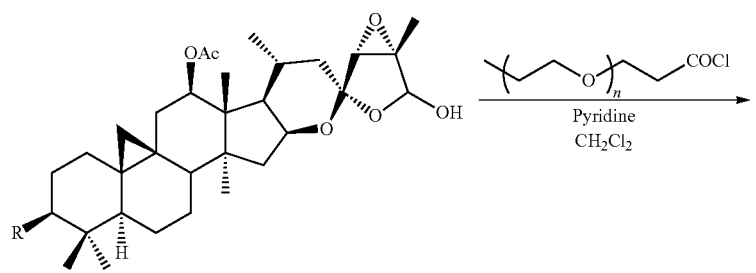
A
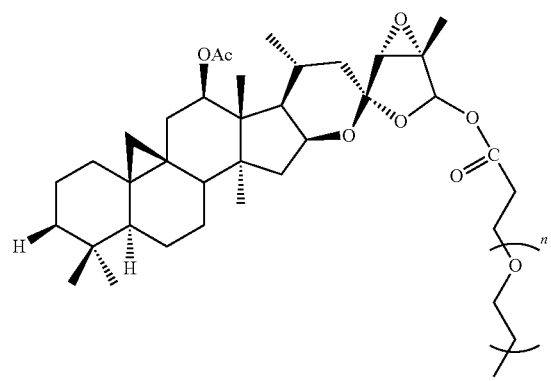
PEG-A Conjugate
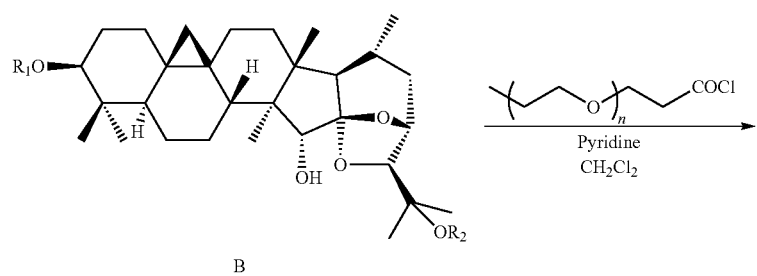
B
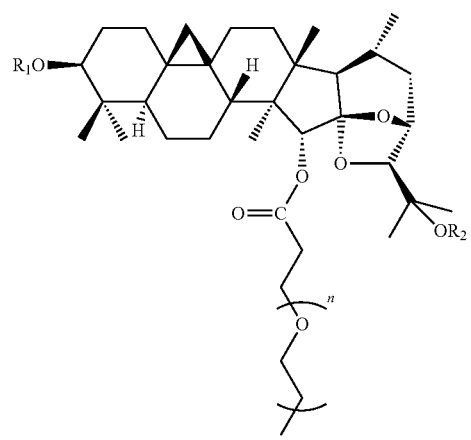
PEG-B Conjugate
| Structure | Compound | R-groups |
|---|---|---|
| A. | Actein | R = OH |
|  | 23-epi-26-deoxyactein | R = H |

| B. | Cimiracemoside C | R1 = α-L-arabinoside; R2 = H |
| | Cimigenoside | R1 = β-D-xyloside; R2 = H |
| | 25-acetylcimigenol xylopyranoside (ACCX) (Qui et al., 2007) | R1 = β-D-xyloside; R2 = Ac |

Preparation of Nanoparticles Containing Actein, Alone, or Combined with Paclitaxel, Coated with Herceptin.

Nanoparticle Encapsulation Strategy

The use of poly(DL-lactic acid) [PLA] polymers and nanoparticles for drug delivery is very attractive because of the excellent biocompatibility and biodegradability of these polymers (Krause et al., 1985, Int. J. Pharm. 27:145-155; De Jaeghere et al., 1999, Pharm. Res. 16:859-866; Nobs et al., Eric Alle'Mann International Journal of Pharmaceutics 250 (2003) 327-337). Antibody targeting PLA nanoparticles have considerably improved the selectivity and bioefficacy (Cirstoiu-Hapcaa et al., European Journal of Pharmaceutical Sciences 38 (2009) 230-237). The procedure developed by Delie and co-workers (Cirstoiu-Hapcaa et al., 2003) is adapted: A series of actein and/or taxol loaded pol(D,L-lactic acid) nanoparticles with varying concentrations of actein and/or taxol is prepared in accordance with Scheme 2 (see FIG. 3). The carboxyl groups on the nanoparticles is covalently modified with cystamine using the carobodiiminde reagent 1-Ethyl-3-(3-dimethylaminopropyl)carbodiimide [EDAC] in accordance with Scheme 2; the resulting nanoparticles is reduced using Tris(2-carboxyethyl)-phosphine hydrochloride [TCEP] to produce nanoparticles which polyvalently display thiol group.

Anti-Her2 specific antibody [trastuzumab, Herceptin®] is covalently modified with the hetero-bifunctional linker m-maleimidobenzoyl-N-hydroxy sulfosuccinimide ester [sulfo-MBS] (the activated NHS ester reacts with lysine groups present on the antibody) (Cirstoiu-Hapcaa et al., 2003; Dolai et al., 2009). Sulfo-MBS activated antibody will be conjugated to the nanoparticles which display thiol groups (NP-SH) in accordance with Scheme 2. (The maleimide group present on the activated antibody reacts with the thiol groups to form a covalent bond (Raja et al., 2007). The unconjugated antibody is removed via centrifugation. The amount of antibody conjugated is determined indirectly by measuring the UV visible spectrum of the supernatant solution after centrifugation using known molar extinction coefficient of the antibody in accordance with the literature reported procedure. All the nanoparticles are characterized via SEM, TEM, AFM and dynamic light scattering. The encapsulation efficiency of the drug molecules is determined using the HPLC assay described in Cirstoiu-Hapcaa et al., (2003). All the equipment necessary for the preparation purification and extensive characterization of the NP-Ab is available at the College of Staten Island.

The antibody targeted bionanoconjugate NP-Ab is used for in vitro studies.

Alternative approach: To enhance the efficacy, nanoparticles containing: 1) PEG-Ac and 2) paclitaxel are prepared. The combination of paclitaxel and actein permits the use of lower doses of the toxic chemotherapy agent paclitaxel.

Actein synergizes with herceptin on apoptosis: To provide further evidence of an interaction with Her2, we tested the effect of actein (2 µg/ml) alone, or combined with the antibody to Her2 Herceptin (trastuzumab) (16 µg/ml), on measures of apoptosis, caspase 3 activity or DNA fragmentation, after treating MDA-MB-453 cells for 48 h. The results are as follows (fold relative to control): for caspase 3: DMSO (control): 1.0; actein: 1.29; Herceptin: 1.284; actein+Herceptin: 1.955 (FIG. 1B); for DNA fragmentation: DMSO (control) 1.0; actein: 0.89; Herceptin: 1.09; actein+Herceptin: 1.34 (p<0.01) (FIG. 3B). Thus, actein induces apoptosis and enhances the apoptotic activity of Herceptin.

Effect of actein on the level of Her2 protein: The effect of actein on the level of Her2 and activated Her2 (p-Her2) protein was examined using Western blot analysis. It was found that actein (40 µg/ml) reduced the level of Her2 (0.72-fold) and p-Her2 (0.37-fold) at 24 h (normalized to β-acetin) (FIG. 2B). The results validate an effect of actein on the Her2 pathway.

Polymer Conjugates. To synthesize more potent cancer cell-targeted derivatives of actein (polymer conjugates), libraries of polymers with various relative loadings of PEG, folate and black cohosh components were generated. Rationale: Actein is highly lipophilic. According to Carl Roth GmbH+Co. KG: Solubility in/Miscibility with water: insoluble.

Among the advantages of polymer drug conjugates are improved in vivo half-lives and improved targeting due to the enhanced permeability and retention effect. The vasculature in tumors is leaky, due to the Enhanced Permeability and Retention (EPR) effect, polymeric drugs such as dendrimers are selectively targeted to the tumors. The folate ligand serves to target polymers to breast cancer cells that overexpress folate receptors (O'Shannessy et al. 2012).

High purity low polydispersity polyacrylic acid (FDA GRAS, Toxipedia) were obtained from Polysciences Inc. to produce polymers that are targeted to breast cancer cells. The polyacrylic acid polymers are subjected to a one-pot three-step esterification reaction in accordance with Scheme 3 (Raja et al., Bioconjugate Chem., 2007, 18 (2):285-288.) See Scheme 3 below.

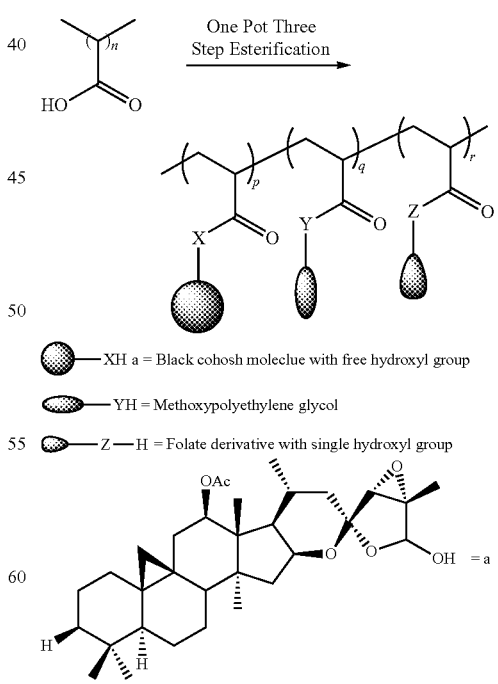

The aglycone is obtained by the hydrolysis of actein with cellulase (Sigma; Onorato and Henion, 2001.). The sequence of polymer modification is the black cohosh molecule first followed by the folate derivative and then large excess of the Monomethoxypolyethylene glycol (~1000 Molecular weight). The final polymers is synthesized and purified in accordance with our recently reported publication (Shi et al., 2009). The link of actein to the polymer is an ester link that would be hydrolyzed by esterases so in that sense it is a prodrug (Langone et al., 2012; 2013).

The final copolymer drug candidate is an improvement from the small molecule because it (a) is selectively targeted to breast cancer cells via the folate ligand, (b) is passively targeted to breast tumors due to the enhanced permeation and retention effect, (c) has improved plasma solubility due to the polyethylene glycol units, (d) has superior pharmacokinetics arising from the fact that Polyethylene glycol is invisible to the immune system (non immunogenic (Raja et al., 2005), and (e) due to its high molecular weight, will not be filtered and removed by the kidneys rapidly. Libraries of polymers with various relative loadings of PEG, folate and black cohosh (actein polymer conjugates) are generated.

Alternate approaches: (1) Replacing the polyethylene glycol units with sugar units to produce neoglycopolymers consisting of the sugar component of the black cohosh component and the folate component in accordance with our recently reported procedures (Raja et al., 2005; Raja et al., Methods in Molecular Biology 751:29-42, 2011). (2) Instead of actein derivative, derivatives of related triterpene glycosides from black cohosh are also prepared.

Actein

Actein targets multiple pathways. Actein preferentially inhibits the growth of malignant cells. Actein also synergizes with Herceptin, as well as paclitaxel. Further, nanoparticle liposomes increase growth inhibitory activity of actein by over fourfold.

In Vitro studies: Numerous studies indicate actein and related herbal components of black cohosh preferentially inhibit the growth of human breast, prostate, oral and skin cancer cells (Einbond, 2009).

The Mechanism of action of actein: In Vitro: Gene expression, RT-PCR, Western blot and siRNA analysis indicated that actein activates the expression of transcription factors that enhance apoptosis and represses the expression of survival and cell cycle genes. In vivo, Actein elicited stress and statin-associated responses in rat liver. It is important that an extract of black cohosh, enriched in triterpene glycosides (27%), induced a dose-related reduction ($p<0.05$) in the incidence of mammary adenocarcinomas in rats, with a protection index of 87.5%, with no adverse effects (Einbond et al., 2012).

Bioavailability: The studies of the present invention indicate actein is bioavailable. Treatment of Sprague-Dawley rats with actein at 35.7 mg/kg resulted in a peak serum level of about 2.4 µg/ml at 6 h (Einbond et al., 2009).

Preparation of Nanoparticles Containing Actein, Alone or Combined with Paclitaxel, Coated with Herceptin.

Nanoparticle Encapsulation Strategy

The use of poly(DL-lactic acid) [PLA] polymers and nanoparticles for drug delivery is attractive because of the excellent biocompatibility and biodegradability of these polymers (Krause et al., 1985; DeJaeghere et al., 1999; Nobs et al., 2003). Antibody targeting PLA nanoparticles have considerably improved the selectivity and bioefficacy (Cirstoiu-Hapcaa et al., 2003). The procedure developed by Delie and co-workers (Cirstoiu-Hapcaa et al., 2003) is adapted: A series of actein and/or paclitaxel loaded pol(D, Llactic acid) nanoparticles with varying concentrations of actein and/or paclitaxel is prepared in accordance with Scheme 2.

The carbonyl groups on the nanoparticles is covalently modified with cystamine using the carobodiiminde reagent 1-Ethyl-3-(3-dimethylaminopropyl)carbodiimide [EDAC] in accordance with scheme 2; the resulting nanoparticles is reduced using Tris(2-carboxyethyl)-phosphine hydrochloride [TCEP] to produce nanoparticles which polyvalently display thiol group.

Tx-Loaded Immunonanoparticle Preparation

Preparation of Plain Poly(Lactic Acid) Nanoparticles.

Plain nanoparticles were prepared by the salting out method, previously described (Nobs, et al. 2003) with slight modifications. To an organic phase consisting of 228 mg of HPLC-grade acetone, and 50 mg of poly(lactic acid) (60 kda), 69.45 mg of poly(vinyl alcohol) (PVA) and 416.7 mg of magnesium chloride hexahydrate ($MgCl_2$) were added, followed by 208 µL of deionized water. This formed an oil in water emulsion which was stirred vigorously at 750 rpm for 10 minutes at 40° C. The aqueous and organic phases were allowed to diffuse together as the emulsion was diluted with 694.4 µL of deionized water, and the solution was allowed to stir for an additional 10 minutes.

Preparation of Tx-Loaded NPs (NP-Tx)

NPs containing Tx were prepared by a salting-out method, as previously described (Nobs et al., 2003) with a slight modification to improve the drug encapsulation efficiency. Briefly, 24 mg of Tx dissolved in 0.5 g acetone was added to a solution of 240 mg poly(dl-lactic acid) (PLA) in 1 g acetone (drug to polymer ratio=1:10). The organic phase was mixed under vigorous stifling (750 rpm) for 10 minutes at 40° C. with 3.5 g of aqueous phase containing 10% (w/w) poly(vinyl alcohol) (PVA) and 60% (w/w) magnesium chloride hexahydrate ($MgCl_2$). The miscibility of the two phases was prevented by the high concentration of salt. Then, 3.5 mL of pure water was added to the NP suspension, and the stirring was maintained for 10 minutes. Excess poly(vinyl alcohol) and magnesium chloride where removed from the suspension by centrifugation at 3,000 rpm for 10 minutes, five times. After preparation and purification, NPs were lyophilized (Edwards, Modulyo, Oberwil, Switzerland) for 2 days in the presence of trehalose (30%, w/w) as a lyoprotector before storage at 4° C. until use.

Thiolation of NPs-Tx.

Thiol functions (—SH) were covalently bound to the NPs-Tx by a two-step carbodiimide reaction, as described previously (Nobs et al., 2003). Briefly, 100 mg of NPs-Tx were suspended in 5 ml water, and the reaction was initiated by consecutively adding 10 ml of a solution of EDAC (24 mg/ml) and 5 ml of a cystamine solution (71 mg/ml corresponding to 896 mol cystamine/mol PLA). The final suspension was completed with water to 25 ml and stirred under mild conditions for 24 h at room temperature. Thereafter, EDAC and non-reacted cystamine were removed by two successive centrifugations (50,000×g for 20 min). NPs were then re-suspended in purified water and incubated for 3 h with 1 ml of an aqueous solution of TCEP (6 mg/ml) to reduce disulfide bonds. Finally, thiolated Tx-loaded NPs (NPs-Tx-SH) were purified by two successive centrifugations (50,000×g for 15 min) and freeze-dried in presence of trehalose (30%, w/w). The concentration of the—SH functions on the surface of NPs was determined spectrophotometrically at $\lambda$=410 nm (Hewlett Packard, Model 8453, Germany) using Ellman's reagent.

Activation of Mab and Covalent Binding to NPs-Tx-SH.

The covalent binding of mAbs to the NPs-Tx-SH was performed according to a previously described method (Nobs et al., 2006). Briefly, 1 ml of clinical grade anti-HER2 (Herceptin®) solution was purified by centrifugation at 4000×g for 15 min (Centaur 2 MSE) using Amicon Ultra-4 centrifugal filter devices. Two milligrams of purified mAbs were activated in PBS (pH 7.4) with sulfo-MBS at a molar ratio 1/20 (mAbs/sulfo-MBS) for 45 min at room temperature. Non-reacted sulfo-MBS was removed by centrifugation (4000×g for 15 min) using Amicon Ultra-4 centrifugal filter devices. Five hundred microliters of activated anti-HER2 (1 mg/ml) was reacted for 1, 6 or 12 h with gentle shaking at room temperature with 500 µ 1 NPs-Tx-SH (20 mg/ml). Unconjugated mAbs were removed by 2 cycles of centrifugation (48,000×g for 10 min) using a Beckman Avanti™ 30 centrifuge (rotor 1202; Beckman Coulter Inc., Fullerton, CA, USA). Finally, NPs-Tx-HER were stored in PBS at 4° C. and used within a week after preparation. The amount of mAb conjugated to NPs was determined indirectly by measuring uncoupled mAb in the supernatant after a centrifugation step. A spectrophotometric method ($\lambda$=280 nm) (Hewlett Packard, Model 8453, Germany) was used by assuming an extinction coefficient of $1.4 M^{-1} cm^{-1}$. The number of mAbs coupled per NP was calculated as previously published (Cirstoiu-Hapca et al., 2007). NPs-Tx-RIT were obtained in the same manner and used as a negative control in further experiments.

Synthesis of Actein-PEG-Succinate Esters
Synthesis of mPEG-Succinate mPEG (100 mmol) was dissolved in 250 mL chloroform and to this resulting solution was added succinic anhydride (125 mmol) and 10 mL pyridine. Then the reaction mixture was refluxed for 48 h with stifling. After evaporation of the reaction mixture to dryness, the residue was dissolved in saturated sodium bicarbonate solution, filtered and then extracted with ethyl acetate (twice, 200 mL each). Aqueous phase was cooled to 0° C. and the pH was adjusted to 2.0 with 2 M hydrochloric acid, and then extracted with methylene chloride (3×200 mL). The methylene chloride solution was dried over magnesium sulfate and then evaporated to dryness.

Synthesis of Actein-PEG-Succinate Esters.

DCC (0.015 mol) and HOBT (0.015 mol) were added to a solution of Actein (0.010 mol) and mPEG-succinate (0.012 mol) in 60 mL DMF. The mixture was stirred at 40 C for 12 h and filtered.

The post-processing method of product: the reaction mixture was filtered. The mixture of acetic acid and tetrahydrofuran (mass ratio: 1:9) were added into the filtrate with stifling for 2 h and then ether was added into the mixture. The precipitate was filtered and purified by silica gel column chromatography ($CH_2Cl_2/CH_3OH$=10:1). Finally, the product was crystallized three times from ethanol and dried under vacuum.

Some embodiments of the present invention include:
A method to improve the bioavailability of a triterpenes glycoside or triterpene comprising covalently modifying the reactive hydroxyl group in compounds A and/or B with polyethylene glycol as follows:

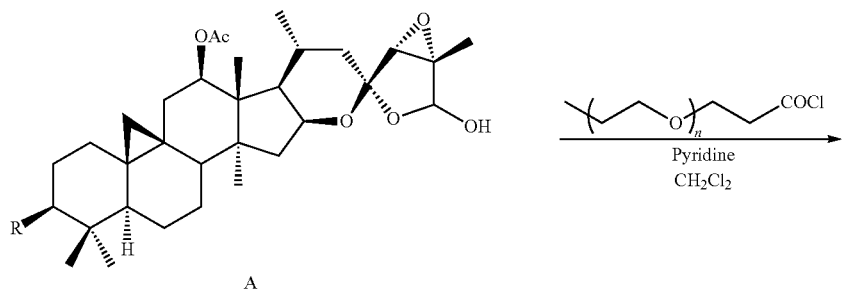

A

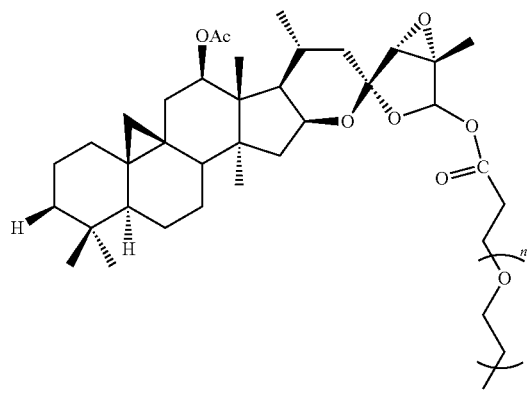

PEG-A Conjugate

-continued

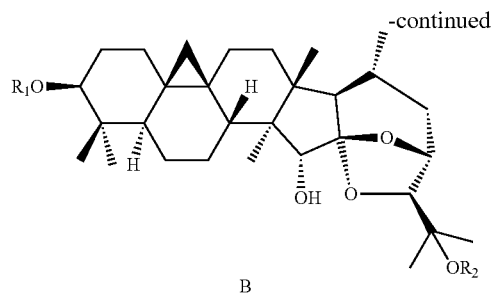 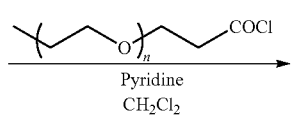

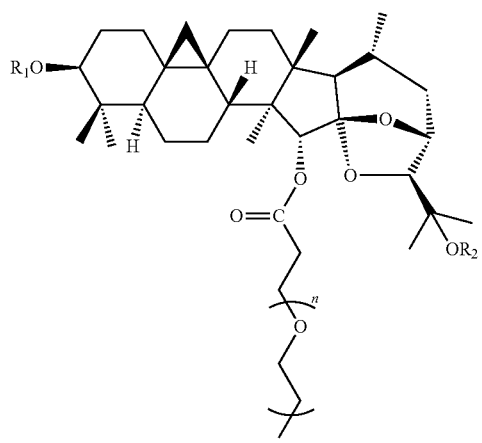

PEG-B Conjugate to prepare a PEGylated triterpenes glycoside,
wherein R is OH or H, and wherein R1 is α-L-arabinoside and R2 is H, R1 is β-D-xyloside and R2 is H, or R1 is β-D-xyloside and R2 is Ac.

A method of forming triterpenes glycoside or triterpene nanoparticles comprising adding actein to poly(DL-lactic acid) in acetone, and isolating actein nanoparticles. The method may further comprise adding a chemotherapeutic agent to the poly(DL-lactic acid) in acetone. The chemotherapeutic agent can be a taxol, and/or Herceptin.

A method of making a chemotherapeutic formulation comprising: providing pol(DL-lactic acid) nanoparticles loaded with a triterpenes glycoside or triterpene; modifying the nanoparticles to produce nanoparticles with thiol groups; and conjugating a sulfo-maleimidobenzoyl-N-hydroxy sulfosuccinimide ester activated antibody to the nanoparticles with the thiol groups, wherein the antibody is anti-Her2, thereby making a chemotherapeutic formulation. The nanoparticles can further be loaded with a taxoid. The triterpenes glycoside can be PEGylated. The nanoparticles with thiol groups can be produced by contacting the nanoparticles with cystamine and 1-ethyl-3-(3-dimethylaminopropyl)carbodiiminde (EDAC) and a reducing agent.

A method of making a chemotherapeutic formulation comprising non-covalently encapsulating black cohosh derivatives and nanoparticle actein coated with Herceptin in an antibody targeted pol(DL-lactic acid) nanoparticles, either alone or in combination with paclitaxel.

The invention claimed is:

1. A method of treating cancer in a patient in need thereof with the administration of nanoparticles of

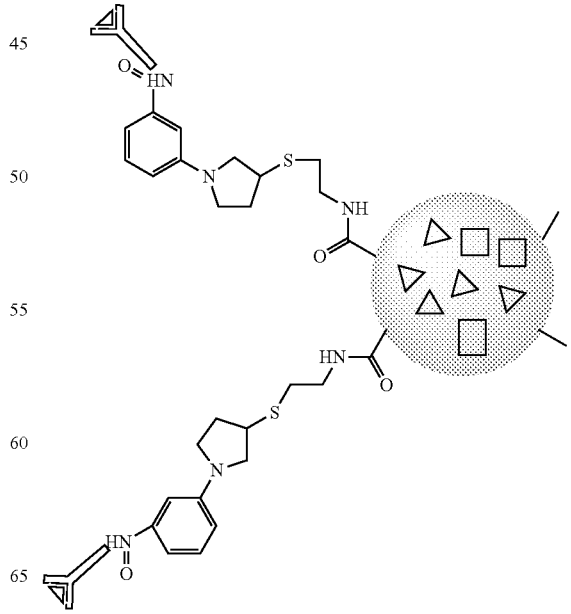

-continued

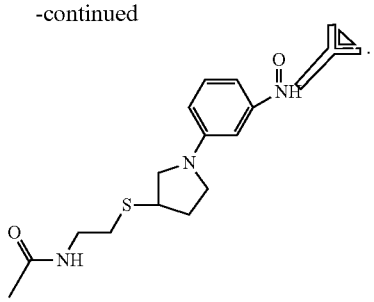

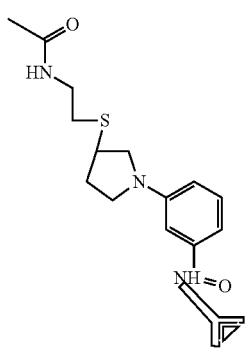

☐ = Chemotherapeutic Agent
▷ = triterpene glycoside or triterpene wherein

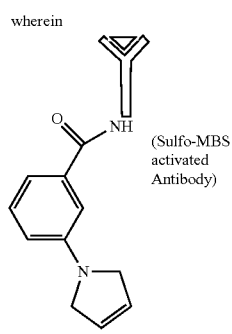
(Sulfo-MBS activated Antibody)

wherein MBS is a maleimidobenzoyl-N-hydroxy sulfosuccinimide ester activated antibody, wherein the sulfo-MBS activated antibody is anti-Her2;

wherein the

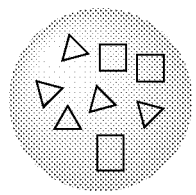

is a poly(DL-lactic acid) nanoparticle loaded with triterpene glycoside or triterpene, wherein ☐ is a chemotherapeutic agent and ▷ is a triterpene glycoside and/or triterpene;

wherein the chemotherapeutic agent is selected from the group consisting of paclitaxel, doxorubicin, 5-FU, trastuzumab, tamoxifen, sulindac sulfide, thapsigargin and MEK inhibitor U0126; and wherein the cancer is selected from the group consisting of breast, prostate, oral, skin, colon and liver cancer.

2. The method of claim 1 wherein the triterpene glycoside is PEGylated.

3. The method according to claim 1 wherein the chemotherapeutic agent is paclitaxel.

4. The method according to claim 1 wherein the chemotherapeutic agent is trastuzumab.

5. The method according to claim 1 wherein the triterpene glycoside is actein.

6. A nanoparticle comprising:
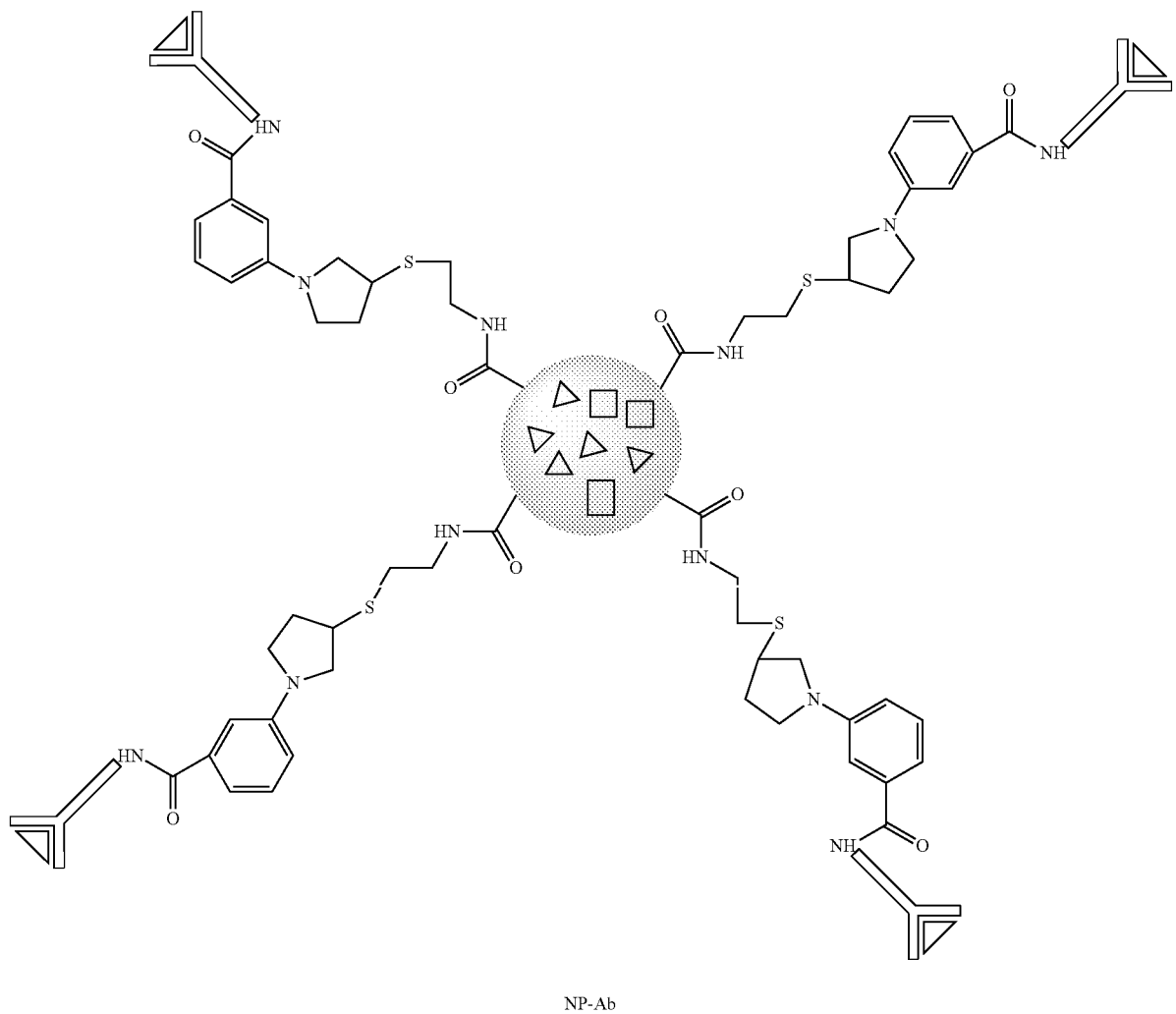
NP-Ab
wherein
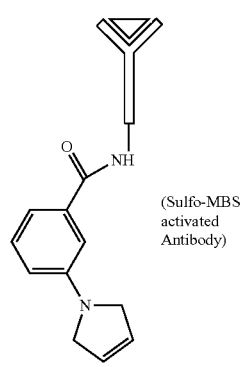
(Sulfo-MBS activated Antibody)
wherein MBS is a maleimidobenzoyl-N-hydroxy sulfosuccinimide ester activated antibody, wherein the sulfo-MBS activated antibody is anti-Her2;
wherein the
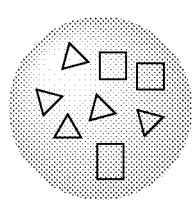

is a poly(DL-lactic acid) nanoparticle loaded with triterpene glycoside or triterpene, wherein □ is a chemotherapeutic agent and ▷ is a triterpene glycoside and/or triterpene; and wherein the chemotherapeutic agent is selected from the group consisting of paclitaxel, doxorubicin, 5-FU, trastuzumab, tamoxifen, sulindac sulfide, thapsigargin and MEK inhibitor U0126.

7. The nanoparticle according to claim 6 wherein the triterpene glycoside is actein.

8. A method of treating cancer in a patient in need thereof with the administration of nanoparticles of

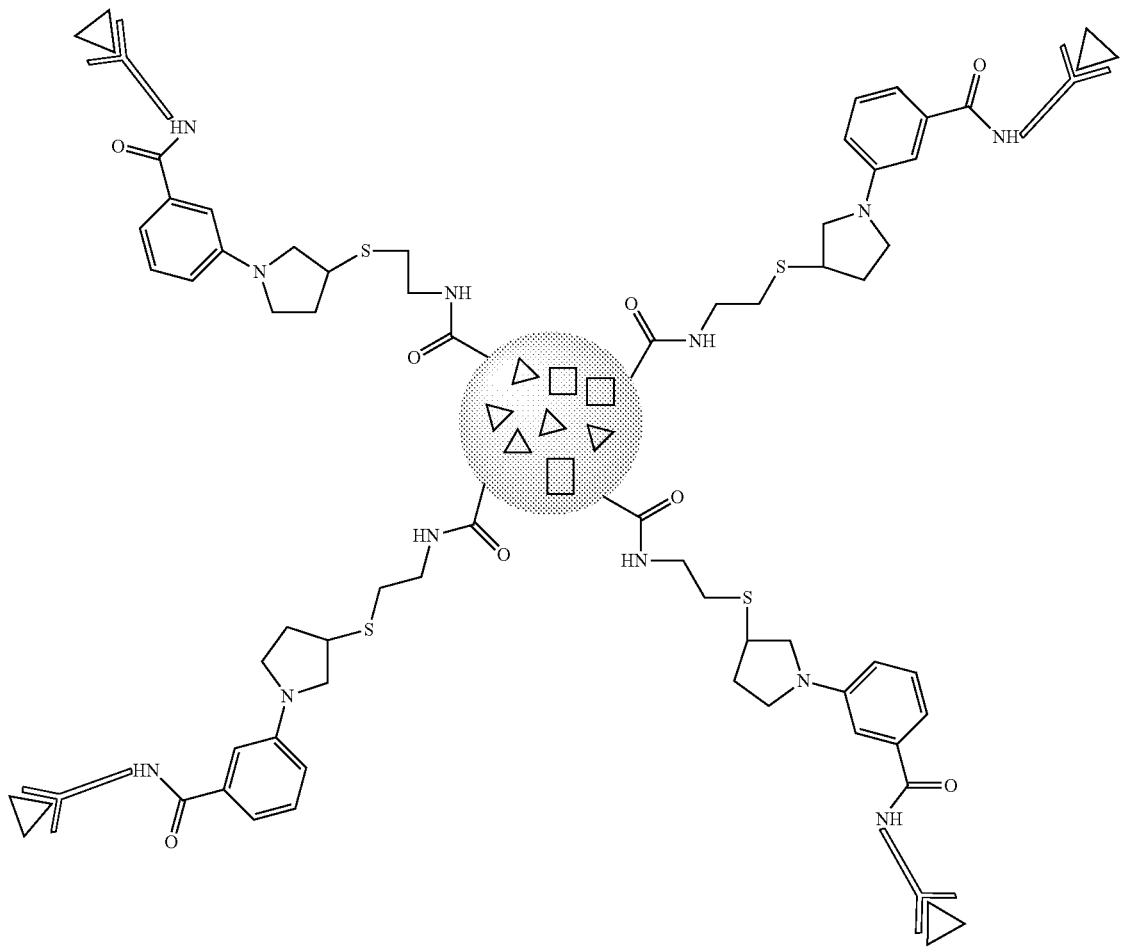

NP-Ab wherein

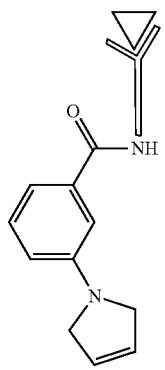

(Sulfo-MBS activated Antibody)

wherein MBS is a maleimidobenzoyl-N-hydroxy sulfosuccinimide ester activated antibody, wherein the sulfo-MBS activated antibody is anti-Her2;
wherein
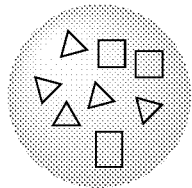
is a poly(DL-lactic acid) nanoparticle comprising paclitaxel (□) and actein (Δ);
wherein the cancer is selected from the group consisting of breast, prostate, oral, skin, colon, and liver cancer.
* * * * *